United States Patent [19]

Kammermeier et al.

[11] Patent Number: 5,359,074

[45] Date of Patent: Oct. 25, 1994

[54] PROCESS FOR THE PREPARATION OF RACEMIC AND OPTICALLY ACTIVE 1,2,3,4-TETRAHYDROISOQUINOLINE-3-CARBOXYLIC ACID AND ITS PRECURSORS

[75] Inventors: Bernhard Kammermeier, Frankfurt am Main; Ulrich Lerch, Hofheim am Taunus, both of Fed. Rep. of Germany

[73] Assignee: Hoechst Aktiengesellschaft, Frankfurt am Main, Fed. Rep. of Germany

[21] Appl. No.: 76,772

[22] Filed: Jun. 15, 1993

Related U.S. Application Data

[62] Division of Ser. No. 822,930, Jan. 21, 1992, Pat. No. 5,252,738.

[30] Foreign Application Priority Data

Jan. 24, 1991 [DE] Fed. Rep. of Germany ....... 4102017

[51] Int. Cl.$^5$ ................. C07D 217/20; C07D 217/18; A61K 31/47
[52] U.S. Cl. ................................................. 546/147
[58] Field of Search ......................... 546/147; 514/307

[56] References Cited

U.S. PATENT DOCUMENTS

| | | | |
|---|---|---|---|
| 5,187,290 | 2/1993 | Gordon | 548/338.1 |
| 5,236,934 | 8/1993 | VanAtten | 514/307 |
| 5,252,738 | 10/1993 | Kammermeier | 546/147 |

Primary Examiner—C. Warren Ivy
Assistant Examiner—D. Margaret M. Mach
Attorney, Agent, or Firm—Finnegan, Henderson, Farabow, Garrett & Dunner

[57] ABSTRACT

A process for the preparation of racemic and optically active 1,2,3,4-tetrahydroisoquinoline-3-carboxylic acid is described, in which dihalo-o-xylylenes are cyclized to dicarboxylic acid esters in basic medium using dialkyl N-acylamidomalonates of the formula $(CO_2R^1)_2CHNHCOR^2$, in which $R^1$ is $(C_1-C_4)$-alkyl and $R^2$ is H, $(C_1-C_4)$-alkyl or $(C_6-C_{12})$-aryl, decarboxylated by basic hydrolysis and subsequent acid work-up and then reacted in acid medium to give (D,L)-1,2,3,4-tetrahydroisoquinoline-3-carboxylic acid, or dihalo-o-xylylenes are cyclized in basic medium to give the dicarboxylic acid esters and these are reacted directly without isolation in a one-pot process to give (D,L)-1,2,3,4-tetrahydroisoquinoline-3-carboxylic acid, if desired the racemic 1,2,3,4-tetrahydroisoquinoline-3-carboxylic acid is reacted with (−)menthol and p-toluenesulfonic acid to give (−)menthyl (D)- or (L)-1,2,3,4-tetrahydroisoquinoline-3-carboxylate, then the diastereomers are separated by column chromatography and subjected to basic hydrolysis to give (D)-or (L)-1,2,3,4-tetrahydroisoquinoline-3-carboxylic acid, or (D,L)-1,2,3,4-tetrahydroisoquinoline-3-carboxylic acid is esterified by means of benzyl alcohol and p-toluenesulfonic acid, reacted with D(−)mandelic acid to give benzyl (D)-1,2,3,4-tetrahydroisoquinoline-3-carboxylate (D)-mandelate and benzyl (L)-1,2,3,4-tetrahydroisoquinoline-3-carboxylate (D)-mandelate or with L(+)mandelic acid to give benzyl (D)-1,2,3,4-tetrahydroisoquinoline-3-carboxylate (L)-mandelate and benzyl (L)-1,2,3,4-tetrahydroisoquinoline-3-carboxylate (L)-mandelate and then the compounds obtained are separated into the optical antipodes by fractional crystallization in an inert solvent and the enantiomers (D)- or (L)-1,2,3,4-tetrahydroisoquinoline-3-carboxylic acid are liberated by basic hydrolysis, the chiral auxiliary reagent being recovered.

9 Claims, No Drawings

PROCESS FOR THE PREPARATION OF RACEMIC AND OPTICALLY ACTIVE 1,2,3,4-TETRAHYDROISOQUINOLINE-3-CARBOXYLIC ACID AND ITS PRECURSORS

This is a division of application Ser. No. 07/822,930, filed Jan. 21, 1992, now U.S. Pat. No. 5,252,738.

DESCRIPTION

The invention relates to a process for the preparation of the compounds of the formulae I, Ia and Ib, and their intermediates.

Compounds of the formula Ia or Ib can be employed instead of natural amino acids in synthetic or semisynthetic peptides or peptide-like compounds, such as, for example, bradykinin antagonists or ACE inhibitors and thereby considerably increase the metabolic stability and potency of these compounds.

The compounds of the formulae I, Ia and Ib are known. According to Chem. Ber. 44, 2030 (1911), the compounds of the formulae I, Ia and Ib are obtained by cyclization of racemic or D- or L-phenylalanine with formaldehyde and conc. hydrochloric acid at boiling heat. This route of synthesis, however, has some serious disadvantages:

Thus, a considerable part of the product is racemized under these drastic experimental conditions, the original optical purity being lost (see J. Amer. Chem. Soc. 84, 4487 (1962)). The enantiomerically pure D- or L-1,2,3,4-tetrahydroisoquinolinecarboxylic acids of the formulae Ia and Ib can then only be obtained by very complicated purification operations (for example repeated recrystallization from a 200-fold amount of ethanol/water 2:1). The yields are correspondingly a moderate 35–40%.

More serious is the formation of the carcinogenic bischloromethyl ether, which is formed in mixtures of hydrochloric acid and formaldehyde during the cyclization of phenylalanine. Bischloromethyl ether also has a carcinogenic effect on humans owing to its alkylating properties (H. G. Neumann in "Allgemeine und spezielle Pharmakologie und Toxikologie [General and specific pharmacology and toxicology]", 4th ed., W. Forth, editor, B. I. Wissenschaftsverlag, Mannheim-Vienna-Zurich, p. 621 ff (1983)) and can lead to malignant tumors in hamsters even after a single exposure of 1 ppm (Arch. Environ. Health 30 (2), 61). The use of the process known from the literature is therefore prohibited for reasons of occupational safety.

The present invention is therefore based on the object of finding processes for the preparation of racemic and enantiomerically pure D- or L-1,2,3,4-tetrahydroisoquinoline-3-carboxylic acid, which do not have the disadvantages described.

This object is achieved according to the invention by the process for the preparation of the compounds of the formulae I, Ia and Ib

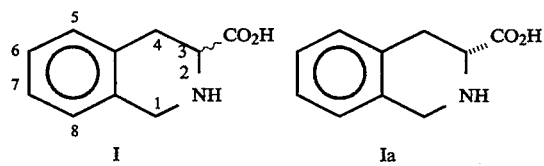

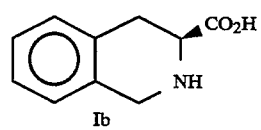

which comprises $a_1$) cyclizing a compound of the formula IVa or IVb

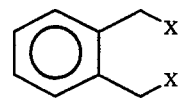

IVa: X = Cl
IVb: X = Br

H with dialkyl N-acylamidomalonates of the formula $(CO_2R^1)_2CHNHCOR^2$ in which $R^1$ is ($C_1$–$C_4$)-alkyl, in particular methyl or ethyl and
$R^2$ is H, ($C_1$–$C_4$)-alkyl or ($C_6$–$C_{12}$)-aryl, in particular methyl and phenyl, in basic medium to give compounds of the formula II

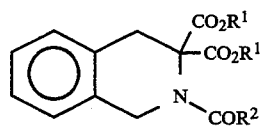

in which $R^1$ and $R^2$ are defined above, decarboxylating the compounds of the formula II thus obtained by basic hydrolysis and subsequent acid work-up to give compounds of the formula III

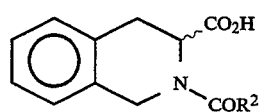

and then reacting in acid medium to give the compound of the formula I, or $a_2$) cyclizing the compounds of the formulae IVa and IVb in basic medium to give the compounds of the formula II and reacting these directly to give the compound of the formula I without isolation in a one-pot process, if desired reacting the racemic compounds of the formula I $b_1$) with (—)menthol and p-toluenesulfonic acid to give a diastereomer pair of the formulae Va and Vb

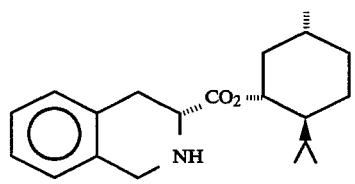

-continued

Vb

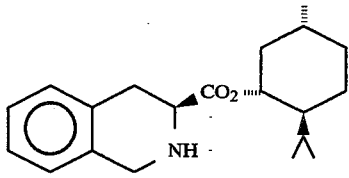

then separating the diastereomers by column chromatography and hydrolyzing by means of a base to give the compounds of the formulae Ia and Ib or b2) esterifying the compound of the formula I by means of benzyl alcohol and p-toluenesulfonic acid to give the compound of the formula VI

VI

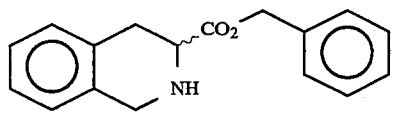

reacting the compound of the formula VI with D(−)mandelic acid to give the compounds of the formulae VIIa or VIIb or with L(+)mandelic acid to give the compounds of the formulae VIIIa and VIIIb VIIa

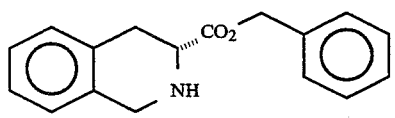

*D(−) mandelic acid

VIIb

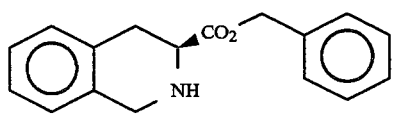

*D(−) mandelic acid

VIIIa

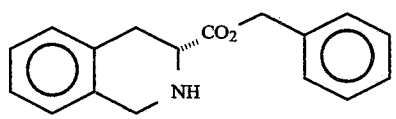

*L(+) mandelic acid

VIIIb

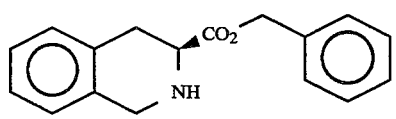

*L(+) mandelic acid then separating the compounds of the formulae VIIa and VIIb or VIIIa and VIIIb into the optical antipodes by fractional crystalization in an inert solvent, such as, for example, methyl, ethyl or butyl acetate, diisopropyl ether or MTB, and liberating the compounds of the formulae Ia and Ib by basic hydrolysis, the chiral auxiliary reagent being recovered.

Important intermediates in these routes of synthesis are dialkyl 1,2,3,4-tetrahydroisoquinoline-N-acyl-3,3-dicarboxylates, 1,2,3,4-tetrahydroisoquinoline-N-acyl-3-carboxylic acids, benzyl (D,L)-1,2,1,4-tetrahydroisoquinoline-3-carboxylate, benzyl (D)-1,2,3,4-tetrahydroisoquinoline-3-carboxylate (D)-mandelate, benzyl(L)-1,2,3,4-tetrahydroisoquinoline-3-carboxylate acid (D)mandelate, benzyl(D)-1,2,3,4-tetrahydroisoquinoline-3-carboxylate (L)mandelate, benzyl(L)-1,2,3,4-tetrahydroisoquinoline-3-carboxylate (L)mandelate, (−)-menthyl (D)-1,2,3,4-tetrahydroisoquinoline-3-carboxylate, (-)-menthyl (L)-1,2,3,4-tetrahydroisoquinoline-3-carboxylate.

(−)-menthyl (D,L)-1,2,3,4-tetrahydroisoquinoline-3-carboxylate.

Starting from the commercially easily available dihalo-o-xylylenes of the formulae IVa and IVb, the dicarboxylic acid ester of the formula II can be prepared in a simple manner by base-catalyzed cyclization in a lower alcohol, preferably methanol, using dialkyl acylamidomalonates, $R^1$ being ($C_1$–$C_4$)-alkyl, in particular methyl or ethyl and $R^2$ being H, ($C_1$–$C_4$)-alkyl or ($C_6$–$C_{12}$)-aryl, in particular methyl and phenyl. Bases which can be used in this cyclization reaction are alkali metal and alkaline earth metal alkoxides, such as sodium methoxide, sodium ethoxide, potassium tert-butoxide or magnesium methoxide, and sodium hydride or alkali metal hydroxides, such as sodium hydroxide or potassium hydroxide. Sodium methoxide is particularly preferred. For larger batches, in particular technical batches, the xylylene IVa is preferred from financial and ecological considerations.

The dicarboxylic acid ester of the formula II is subjected to basic hydrolysis using alkali metal hydroxides, preferably sodium hydroxide, at 20°-90° C. and to acid work-up using strong acids. The racemic N-acyl-α-aminocarboxylic acid of the formula III is obtained with decarboxylation at room temperature and, after treatment with a strong acid, is deacylated to give the racemic compound of the formula I. A strong acid is in general understood as meaning HCl, HBr, $H_2SO_4$ and $H_3PO_4$, in particular HCl. P A one-pot process for the synthesis of the compound of the formula I is particularly preferred in which the dichloroxylylene IVa is cyclized in the manner described above to the diester II and the latter, after treatment with strong aqueous acid, such as, for example, HCl, is converted immediately into the compound of the formula I without isolation.

The reaction is in particular carried out in this case by removing the solvent, preferably methanol, after cyclization in vacuo at 15-60 torr, preferably 25 torr, and heating the solid residue, consisting of NaCl, diester of the formula II and small amounts of by-product, to reflux with half-concentrated hydrochloric acid for several hours. After the reaction time has ended, the mixture is adjusted to pH 4.5 to 7, the product of the formula I precipitating. The yields of this one-pot synthesis are 65% of theory over all stages and are thus superior to the stepwise synthesis with about 70-80% of theory, ≧75% of theory and about 70-80% of theory on the isolated compounds II, III and I. Moreover, the reaction can be carried out more simply and the expenditure in terms of apparatus and personnel is substantially reduced.

The α-aminocarboxylic acid of the formula I obtained in racemic form can be separated by esterification with (−)menthol, as is described in a similar manner for other neutral α-amino acids in Chem. Comm. 18, 421 (1965). Preferably, however, the α-aminocarboxylic acid of the formula I is reacted under acid catalysis, in particular with anhydrous p-toluenesulfonic acid in inert solvents distilling azeotropically with water, such as benzene, toluene or xylene, with at least 1.5 equivalents of (−)menthol at 70° C. up to the boiling temperature of the solvent to give a mixture of the diastereomeric (−)-menthyl esters Va and Vb. The yields are about 80% of theory and are strongly dependent on the duration of the reaction, which is between 30 and 60 hours. The crude product, together with excess (−)menthol, is separated on a chromatography column (for example silica gel column: 30–70 μm) into the diastereomerically pure components Va and Vb using slightly polar eluting agents, such as, for example, cyclohexane/ethyl acetate, ethyl acetate/toluene, diisopropyl ether/toluene or hexane/MTB ether in the ratio 80:20 to 20:80, preferably 50:50, if desired also as gradients. Excess menthol can be recovered from the first fractions in each case.

The respective enantiomerically pure aminocarboxylic acid Ia or Ib

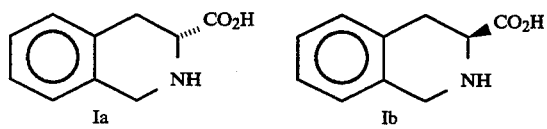

is liberated from the diastereomerically pure menthyl esters Va and Vb by treatment with bases such as sodium hydroxide solution or potassium hydroxide solution in aqueous medium, or aqueous-alcoholic medium, such as, for example, water/$C_1$-$C_3$alkyl alcohol, in the temperature range from room temperature to 90° C. The compounds Ia and Ib precipitate here in yields of about 80% of theory and in enantiomeric purities of ee >99% after establishing a pH between 4.5 and 7.0. Further chemical purification, for example by recrystallization, is unnecessary.

A particularly preferred route for the resolution of the racemate of the formula I into the optical antipodes of the formulae Ia and Ib comprises converting the compound of the formula I into the benzyl ester of the formula VI, as is described in a similar manner for the compounds Ia and Ib in Chem. Pharm. Bull 31 (1), 312 (1983).

The acid-catalyzed esterification, preferably using anhydrous p-toluenesulfonic acid, is in turn carried out at reflux temperature using 3–5 equivalents of benzyl alcohol in solvents distilling azeotropically with water, such as toluene or xylene. The water of reaction formed is collected continuously in a water separator during the 8–12 hours' course of the reaction and indicates the progress of the reaction. The racemic benzyl ester of the formula VI is preferably obtained as the p-toluenesulfonic salt and is liberated from this by treatment with aqueous base solutions, preferably alkali metal carbonate solutions, in water-immiscible organic solvents, preferably ethyl acetate. After phase separation, the organic phase is in each case treated with equimolar amounts of D(−) or L(+)mandelic acid, after which the salt pairs of the formulae VIIa and VIIIb, in each case more sparingly soluble, crystallize out with diastereomer excesses of de >98% and chemical yields of >80% of theory. The residues remaining in the mother liquor of the diastereomeric salts of the formulae VIIb and VIIIa, in each case more readily soluble, crystallize out after continuous addition of a less polar solvent, preferably diisopropyl ether, or by double decomposition with the other mandelic acid enantiomer in each case, with diastereomer excesses of de =94–99% and chemical yields of >70% of theory. From the pure diastereomeric salts of the formulae VIIa, VIIb, VIIIa or VIIIb, the compound of the formula Ia or Ib can be liberated by basic hydrolysis using 1.0–1.1 equivalents of alkali metal hydroxides, preferably sodium hydroxide, and precipitated at pH 4.5–7 and at temperatures between 0° C. and 25° C. in purities of ee >99% and chemical yields of about 95% of theory. The chiral auxiliary reagent can be recovered from the mother liquor by acidification and extraction.

In the process according to the invention, the optical resolution is carried out under mild conditions, such as, for example, at 10° C. to room temperature, by fractional crystallization with later recovery of the chiral auxiliary (D)- or (L)-mandelic acid.

Optical resolution at the stage of the racemic compound of the formula VI without an optically active auxiliary reagent, for example by simple recrystallization, can also not be achieved by seeding with an optically pure isomer of the compound of the formula VI. The enantiomer excesses after crystallization of 20–60% of the material are in the range ee <5%.

Cleavage of these enantiomers at this stage can obviously only be achieved if the enantiomer excesses of the crude material employed for the crystallization are already considerable, for example ee >80%, as described in Chem. Pharm. Bull. 31 (1), 312 (1983).

The process according to the invention is thus superior in every respect to the old Pictet-Spengler cyclocondensation using formaldehyde and concentrated hydrochloric acid. It represents a great advance compared to the prior art, since the disadvantages mentioned of the partial racemization of the expensive starting materials and the formation of a highly toxic by-product of the old process are avoided in particular.

The examples which follow are intended to illustrate the invention in greater detail.

EXAMPLE 1

D,L-1,2,3,4-Tetrahydroisoquinoline-3-carboxylic acid

Method A: (compound I from compound IVa)

5.00 kg of α,α'-dichloro-o-xylylene (compound IVa) and 6.20 kg of diethyl acetamidomalonate are introduced into 49 l of methanol with stirring at room temperature and 5.14 kg of sodium methoxide solution (30% by weight in methanol) are metered in during the course of 30 minutes, the reaction mixture simultaneously being heated to reflux.

After addition is complete, the mixture is stirred under reflux for 10 minutes and a further 5.14 kg of sodium methoxide solution are then metered in under reflux during the course of 2 hours. The mixture is then stirred under reflux for 2 hours and finally concentrated to dryness and the residue is treated with 43 l of half-concentrated hydrochloric acid and again stirred under reflux for 4 hours. During the course of this, the mixture begins to foam vigorously (decarboxylation), the evolution of gas increasing after 2 hours.

After the reaction time has ended, the mixture is stirred at room temperature for 15 hours, then cooled to 0° C., adjusted to pH 6.5 with cooling using 25% ammonia solution, stirred at 0° C. for a further hour and filtered off with suction. The residue is washed with 2·2 l of water and dried in a drying oven at 60° C. (Karl-Fischer titration after drying for 12 hours gives a residual water content of 0.06%).

Yield: 3.27 kg (65% of theory over all stages)
Melting point: >300° C.
TLC: silica gel, Merck; ethyl acetate (EA)/MeOH/glacial acetic acid/$H_2O$ 70:30:5:5 $R_1$:0.3 (staining with ninhydrin)
$^1$H-NMR($CF_3CO_2D$, 270 MHz): $\delta = 3.51$ and 3.66 (2·dd, 2H, $J_{gem} = 18$ Hz, 9 Hz, 6 Hz; $CH_2$—CH); 4.64—4.78 (m, 3H, $CH_2$—C$\underline{H}$ and $CH_2$—N); 7.24–7.48 (m, 4aromatic H).

Method B: (compound I from compound III)

7.6 g of (D,L)-1,2,3,4-tetrahydroisoquinoline-N-acetyl-3-carboxylic acid (compound III) are suspended in 50 ml of half-concentrated hydrochloric acid and stirred under reflux for 4 hours. The mixture is then cooled to 0° C., adjusted to pH 6.5 using 25% ammonia solution, stirred at 0° C. for a further hour and filtered off with suction. The residue is washed with 2·10 ml of water, sucked dry and dried in a vacuum desiccator.

Yield: 3.6 g (78% of theory).
Physical data: see under method A.

EXAMPLE 2

Dimethyl 1,2,3,4-tetrahydroisoquinoline-N-acetyl-3,3-dicarboxylate (compound II from compound IVb)

18 ml of sodium methoxide solution (30% by weight in methanol) are added dropwise at room temperature during the course of 10 minutes to a stirred suspension of 26.4 g of $\alpha,\alpha'$-dibromo-o-xylylene (compound IVb) and 21.7 g of diethyl acetamidomalonate in 175 ml of methanol and the mixture is then heated to reflux.

After refluxing for 15 minutes, a further 18 ml of sodium methoxide solution are metered in during the course of 2 hours and, after addition is complete, the mixture is additionally stirred at reflux temperature for a further 2 hours (the pH then indicates neutrality). For working-up, the mixture is concentrated to dryness, the residue is partitioned between 100 ml of water and 150 ml of ethyl acetate and the phases are separated. The aqueous phase is extracted using 2·75 ml of ethyl acetate and the combined organic phases are washed with 1·100 ml of half-concentrated sodium chloride solution, dried over $Na_2SO_4$ and concentrated to dryness. The residue is dissolved and allowed to crystallize from 100 ml of methyl tert-butyl ether (MTB ether)/diisopropyl ether (1:1).

Yield: 21.5 g (75% of theory)
Melting point: 141°–143° C.
TLC: silica gel, Merck; MTB ether $R_1$:0.3
$^1$H-NMR ($CDCl_3$, 270 MHz); $\delta = 2.30$ (s, 3H, NCO—$CH_3$); 3.43 (s, 2H, $CH_2$—C); 3.68

EXAMPLE 3

D,L-1,2,3,4-Tetrahydroisoquinoline-N-acetyl-3-carboxylic acid (compound III from compound II)

A suspension of 10.65 g of dimethyl 1,2,3,4-tetrahydroisoquinoline-N-acetyl-3,3-dicarboxylate (compound II) in a solvent mixture of 100 ml of methanol and 20 ml of water is treated at room temperature with 4.55 g of potassium hydroxide pellets in portions and then heated to reflux for 4 hours, after which a clear solution is formed.

The reaction solution is concentrated to dryness after cooling to room temperature, and the residue is treated with 100 ml of ethyl acetate and adjusted to pH 1 using 2 N hydrochloric acid with vigorous stirring (evolution of gas).

After phase separation, the aqueous phase is extracted with 3·50 ml of ethyl acetate, and the combined organic phases are dried over $Na_2SO_4$ and concentrated to dryness. The residue is made into a paste with 10 ml of MTB ether and finally sucked dry.

Yield: 6.84 g (85% of theory)
Melting point: 171°–173° C. (lit: 171°–172° C.)[1]
[1]Chem. Pharm. Bull. 16(3), 414 (1968)
TLC: silica gel, Merck; ethyl acetate/MeOH/glacial acetic acid/$H_2O = 70:30:5:5$ $R_1$:0.7
$^1$H-NMR ($d_6$-DMSO, 270 MHz); $\delta = 2.07$ and 2.16 (2·s, 3H, NCO$CH_3$, coalescence temp.: 90° C.); 3.00–3.29 (m, 2H, $CH_2$—CH); 4.31, 4.62, 4.74 and 4.75 (2·2·d, 2H, J = 18 Hz, 16 Hz, $CH_2$—N); 4.98 and 5.16 (2·dd, 1H, J = 6 Hz, 4 Hz, $CH_2$—C$\underline{H}$); 7.13–7.25 (m, 4H, aromatic H); 12.7 (broad, 1H, $CO_2\underline{H}$).

EXAMPLE 4

(—)Menthyl (D)- and (L)-1,2,3,4-tetrahydroisoquinoline-3-carboxylates (compounds Va and Vb from compound I)

10 g of p-toluenesulfonic acid monohydrate are suspended in 150 ml of toluene with stirring and the mixture is heated to reflux for 1 hour in a water separator (50 ml of toluene and 1 ml of water then remain in the water separator).

The mixture is then cooled to 80°–90° C., successively treated with 6.3 g of D,L-1,2,3,4-tetrahydroisoquinoline-3-carboxylic acid (compound I) and 8.3 g of (—)menthol and then heated to reflux in a water separator for a further 30 hours (after this time a further 1.3 ml of water have separated). The brown reaction solution is cooled to room temperature and washed with 2·75 ml of 2N sodium bicarbonate solution. The combined aqueous phases are washed with 1·50 ml of saturated sodium chloride solution.

The organic phase is dried over $Na_2SO_4$ and concentrated to dryness, after which 10.3 g of oily crude product remain. The crude product is purified on a chromatography column over 300 g of silica gel (30–70 μm) using the solvent mixture cyclohexane/ethyl acetate (7:3) and separated into the two diastereomers.

Yields: 1.2 g of recovered (—)menthol 4.6 g of compound Vb (83% of theory); $[\alpha]_D^{20} = -117.2°$ (c=1, MeOH)
4.2 g of compound Va (76% of theory); $[\alpha]_D^{20} = -10.5°$ (c=0.5, MeOH)
TLC: silica gel, Merck; toluene/ethyl acetate 1:1 $R_1$: 0.9 ((—)menthol) 0.6 (compound Vb) 0.5 (compound Va)
$^1$H-NMR ($d_6$-DMSO, 270 MHz, compound Vb): $\delta = 0.71$ (d, 3H, J = 7 Hz; $(CH_2)_2 = CH$—$CH_3$); 0.84–0.92 (m, 6H, CH($CH_3$)$_2$); 0.77–1.13, 1.25–1.55, 1.58–1.71 and 1.78–1.90 (4·m, 9H, cyclo—$CH_2$—CH—$CH_2$—$CH_2$—CH(C$\underline{H}$)—C(O)); 2.78 and 2.93 (2·dd, 2H, $J_gem = 16$ Hz, 10 Hz, 5 Hz; C$\underline{H}$—CH(N)); 3.64 (dd, 1H, J = 10 Hz, 5Hz; CH-N); 3.90 and 3.95 (2·d, 2H, J = 16 Hz; $CH_2$—N); 4.66 (dt, 1H, J = 11 Hz, 4 Hz, CH—O); 7.00–7.15 (m, 4H, aromatic H).
$^1$H-NMR ($d_6$-DMSO, 270 MHz, compound Va): $\delta = 0.64$ (d, 3H, J = 7 Hz; (CH2)$_2 = CH$—$CH_3$); 0.82–0.90 (m, 6H, CH($CH_3$)$_2$); 0.77–1.11, 1.22–1.55, 1.58–1.92 (3·m, 9H, cyclo-$CH_2$—CH—$CH_2$—CH$_2$—CH(C$\underline{H}$)—C—(O)—); 2.82 and 2.94 (2·dd, 2H, $J_{gem} = 16$ Hz, 10 Hz, 5 Hz; $CH_2$—CH(N)); 3.67 (dd, 1H, J=10 Hz, 5 Hz; CH—N); 3.88 and 3.95 (2·d, 2H, J=16 Hz; $CH_2$—N); 4.62 (dt, 1H, J=11 Hz, 4 Hz; CH—O); 6.98–7.13 (m, 4H, aromatic H).

EXAMPLE 5

D-1,2,3,4-Tetrahydroisoquinoline-3-carboxylic acid (compound Ia from compound Va)

1.1 g of (−)menthyl D-1,2,3,4-tetrahydroisoquinoline-3-carboxylate (compound Va) are introduced at 0° C., treated with a solution of 210 mg of NaOH in 12 ml of methanol, likewise cooled to 0° C., and stirred at this temperature for 5 minutes. The mixture is then heated to room temperature, stirred for a further 5 hours and finally brought to pH 7 by addition of 2N hydrochloric acid.

To complete crystallization, the mixture is allowed to stand at room temperature, without stirring, for 12 hours, and the compound is then filtered off with suction, washed with 5 ml of water and dried in vacuo at room temperature.

Yield: 515 mg (83% of theory)
$[\alpha]_D^{20} = 130°$ (c=1; 0.1N HCl); ee>99% (GC, cyclodextrin column)
Melting point: 321°–323° C.
TLC: silica gel, Merck; ethyl acetate/MeOH/glacial acetic acid/$H_2O$ = 70:30:5:5 $R_1$:0.3 (staining with ninhydrin)
$^1$H-NMR analogous to compound I

EXAMPLE 6

Benzyl D,L-1,2,3,4-tetrahydroisoquinoline-3-carboxylate (compound VI from compound I)

190.2 g of p-toluenesulfonic acid monohydrate are suspended in 3 l of toluene with stirring and heated to reflux in a water separator for 1 hour. The temperature is then reduced to 80°–90° C., 177.2 g of D,L-1,2,3,4-tetrahydroisoquinoline-3-carboxylic acid are introduced and the mixture is heated to reflux for a further hour (80 ml of toluene and 22 ml of water then remain in the water separator).

300 ml of benzyl alcohol are then added dropwise to the reaction solution during the course of 30 minutes and, after addition is complete, the mixture is heated to reflux in a water separator for a further 10 hours. The clear brown reaction solution is concentrated to dryness and then stirred with 2 l of ethyl acetate and 1 l of diisopropyl ether, after which the product begins to crystallize out spontaneously. The mixture is treated with a further 2 l of diisopropyl ether with stirring, stirred at 0° C. for 2 hours and filtered off with suction. The residue is washed with 100 ml of diisopropyl ether and sucked dry. The residue is dried in vacuo at room temperature.

Yield: 346.5 g (79% of theory of VI.toluenesulfonic acid)
Melting point: 128°–130° C.
TLC: silica gel, Merck; ethyl acetate/MeOH/glacial acetic acid/$H_2O$=70:30:5:5 $R_1$:0.8
$^1$H-NMR ($d_6$-DMSO, 270 MHz); $\delta$=2.29 (s,3H, tosyl $CH_3$); 3.15 and 3.36 (2·dd, 2H, $J_{gem}$=18 Hz, 12 Hz, 5 Hz; $CH_2$—CH); 4.34 and 4.40 (2·d, 2H, J=16 Hz; $CH_2$—N); 4.67 (dd, 1H, J=11 Hz, 4 Hz; CH-N); 5.32 (s, 2H, CHphenyl); 7.11 and 7.47 (2·d, 4H, J=8 Hz; tosyl H); 7.23–7.31 (m, 4H, phenylene-H); 7.36–7.46 (m, 5H, phenyl-H); 9.70 (broad, 2H, $NH_2^+$).

Compound VI is liberated from its tosylate adduct in quantitative yield as a colorless oil by treatment with saturated sodium bicarbonate solution and ethyl acetate extraction:

$^1$H-NMR ($d_6$-DMSO, 270 MHz); $\delta$=2.86 and 2.98 (2·dd, 2H, $J_{gem}$=16 Hz, 10 Hz, 5 Hz; $CH_2$—CH); 3.77 (dd, 1H, J=12 Hz, 4 Hz; CH—N); 3.89 and 3.96 (2·d, 2H, J=16 Hz, $CH_2$—N); 5.17 (s, 2H, $CH_2$—phenyl); 7.00–7.15 (m, 4H, phenylene-H); 7.31–7.42 (m, 5H, phenyl-H).

EXAMPLE 7

Benzyl (D)-1,2,3,4-tetrahydroisoquinoline-3-carboxylate (D)-mandelate and benzyl (L)-1,2,3,4-tetrahydroisoquinoline-3-carboxylate (D)-mandelate (compounds VIIa and VIIb from compound VI)

A suspension of 109.9 g of benzyl (D,L)-1,2,3,4-tetrahydroisoquinoline-3-carboxylate tosylate in 500 ml of ethyl acetate is adjusted to between pH 7.0 and 7.5 with stirring and continuous pH control at room temperature using saturated sodium bicarbonate solution and the phases are then separated. The water phase is extracted with 100 ml of ethyl acetate and the combined organic phases are washed with 100 ml of water. The ethyl acetate phase is dried over $Na_2SO_4$ and filtered, and the drying agent residue is washed with 2·50 ml of ethyl acetate. The filtrate is treated with a total of 38.04 g of D(−)mandelic acid in portions and stirred at room temperature for 12 hours and 0° C. for 1 hour. The colorless crystal magma precipitated is then filtered off with suction, washed with 50 ml of ethyl acetate and 50 ml of diisopropyl ether and dried in a vacuum desiccator to constant weight.

Remaining (L,D)-diastereomeric salt (compound VIIb) crystallizes out after concentrating the mother liquor to about 30% of the original volume and stirring at room temperature for 10 hours. The mixture is treated with 150 ml of diisopropyl ether and stirred briefly, and the crystal magma is filtered off with suction and sucked dry.

Yield: 46.6 g of compound VIIa (89% of theory of (D,D)-diastereomer)
$[\alpha]_D^{20}$=+11.7° (c=1, MeOH); de>98% (HPLC after derivatization) Melting point: 98°–100° C.

Yield: 42.3 g of compound VIIb (81% of theory of (D,L)-diastereomer) $[\alpha]_D^{20}$=−99.6° (c=0.5 MeOH); de>96% (HPLC after derivatization) Melting point: 84°–87° C.

$^1$H-NMR ($d_6$-DMSO, 270 MHz, compound VIIa): $\delta$=2.88 and 3.02 (2·dd, 2H, $J_{gem}$=16 Hz, 10 Hz, 5 Hz; $CH_2$—CH); 3.83 (dd, 1H, J=11 Hz, 4 Hz; CH—N); 3.94 and 4.00 (2 d, 2H, J=16 Hz; $CH_2$—N); 4.98 (s, 1H, phenyl-CH—O); 5.18 (s, 2H, phenyl—$CH_2$—O); 7.02–7.15 (m, 4H, phenylene-H); 7.20–7.47 (m, 10H, phenyl-H).

$^1$H-NMR (compound VIIb) identical to compound VIIa.

EXAMPLE

Benzyl (D)-1,2,3,4-tetrahydroisoquinoline-3-carboxylate (L)-mandelate

Benzyl (L)-1,2,3,4-tetrahydroisoquinoline-3-carboxylate (L)-mandelate

Method A (compounds VIIIa and VIIIb from compound VI)

11 g of benzyl (D,L)-1,2,3,4-tetrahydroisoquinoline-3-carboxylate tosylate are suspended in 50 ml of ethyl acetate and adjusted to between pH 7.0 and 7.5 with saturated sodium bicarbonate solution with stirring at room temperature, and the phases are then separated. The water phase is extracted with 10 ml of ethyl acetate and the combined organic phases are washed with 10 ml of water. The organic phase is dried over $Na_2SO_4$ and filtered, and the drying agent residue is washed with 10 ml of ethyl acetate. The filtrate is treated in portions with 3.8 g of L(+)mandelic acid and stirred at room temperature for 12 hours. The precipitate is then filtered off with suction, washed with 20 ml of diisopropyl ether and dried to constant weight. The mother liquor obtained is concentrated to about 30% of the original volume to crystallize the (D,L)-diastereomeric salt (compound VIIIa) remaining therein and stirred at 0° C. for a further 3–4 hours, and the thick crystal magma formed is treated with 10 ml of ethyl acetate and 20 ml of diisopropyl ether. After stirring at room temperature for 15 minutes, the compound is filtered off with suction and sucked dry.

Yield: 4.30 g of compound VIIIb (82% of theory of (L,L)-diastereomer)

$[\alpha]_D^{20} = +12.7°$ (c=1, MeOH); de>98% (HPLC after derivatization) Melting point: 99°–101° C.

Yield: 3.80 g of compound VIIIa (72% of theory of (D,L)-diastereomer) $[\alpha]_D^{20} = -99.8°$ (c=1 MeOH); de>98% (HPLC after derivatization) Melting point: 85°–87° C.

$^1$H-NMR (d$_6$-DMSO, 270 MHz, compounds VIIIa and VIIIb) is identical to the corresponding spectrum of the compound VIIa.

Method B (compound VIIIa and VIIIb from compound VI)

110 g of benzyl (D,L)-1,2,3,4-tetrahydroisoquinoline-3-carboxylate tosylate are suspended in 350 ml of ethyl acetate, treated at room temperature with stirring with 150 ml of saturated sodium bicarbonate solution and 50 ml of water, and the phases are separated after 10 minutes. The organic phase is washed again with 100 ml of half-saturated sodium bicarbonate solution, the phases are separated and the combined water phases are extracted with 150 ml of ethyl acetate. The combined ethyl acetate phases are dried over $Na_2SO_4$ after washing with 100 ml of saturated sodium chloride solution, filtered and treated with 38 g of L(+)mandelic acid with stirring.

Crystallization begins about 5 minutes after the addition, and is completed by stirring at room temperature for 10 minutes and then stirring at 0° C. for one hour. The crystal magma is filtered off with suction and washed with a little ethyl acetate and 100 ml of diisopropyl ether, and compound VIIIa is dried to constant weight. The mother liquor remaining is washed with sodium bicarbonate solution analogously to the procedure described above, dried over $Na_2SO_4$, filtered and treated with 18 g of D(−)mandelic acid with stirring. The solution is stirred at room temperature for 5 minutes and at 0° C. for 1 hour, then the crystal magma is filtered off with suction, washed with a little ethyl acetate and 50 ml of diisopropyl ether and sucked dry.

Yield: 50.0 g of compound VIIIb (95% of theory of (L,L)-diastereomer)

$[\alpha]^0 = -13.3°$ (c=1, MeOH); de>98% (HPLC after derivatization)

Yield: 44.6 g of compound VIIIa (85% of theory of (D,D)-diastereomer) $[\alpha]_D^{20} = -14.3°$ (c=1 MeOH); de>99% (HPLC after derivatization)

EXAMPLE 9a (D)-1,2,3,4-Tetrahydroisoquinoline-3-carboxylic acid (compound Ia from compound VIIa)

A solution of 8.4 g of NaOH in 200 ml of water is metered during the course of 10 minutes into a suspension, stirred at room temperature, of 40 g of benzyl (D)-1,2,3,4-tetrahydroisoquinoline-3-carboxylate (D)mandelate in 200 ml of water and the reaction mixture is then additionally stirred for 9 hours.

The clear solution is adjusted to pH 7 using 2N hydrochloric acid, the product precipitating. The mixture is stirred for 30 minutes and left without stirring at room temperature for 12 hours to complete crystallization, and the crystal magma is then filtered off with suction.

The residue is made into a paste with 2·15 ml of ethyl acetate, sucked dry and dried in vacuo at room temperature. The two-phase mother liquor is adjusted to pH 1 using conc. hydrochloric acid and extracted with 2·150 ml of ethyl acetate. The combined organic phases are washed with 1·50 ml of saturated sodium chloride solution, separated from the aqueous phase, dried over $Na_2SO_4$ and concentrated to dryness. The residue is made into a paste with 10 ml of toluene, sucked dry and recrystallized from 20 ml of water.

Yield (compound Ia): 15.0 g (89% of theory); Melting point: 321°–325° C.;

$[\alpha]_D^{20} = 130°$ (c=1, 0.1 N HCl); ee>99% (GC, cyclodextrin column)

Yield (D(−)mandelic acid): 8.9 g (62%)

$[\alpha]_D^{20} = -155.7°$ (c=5; H$_2$O) [lit.: −155±5°]

EXAMPLE 9b

L-1,2,3,4-Tetrahydroisoquinoline-3-carboxylic acid (compound Ib from compound VIIIb)

2.7 g of benzyl (L)-1,2,3,4-tetrahydroisoquinoline-3-carboxylate (L)-mandelate are suspended in 50 ml of ethyl acetate and washed with 2·75 ml of saturated sodium bicarbonate solution. The combined aqueous phases[2] are extracted with 30 ml of ethyl acetate and the combined organic phases are washed with 50 ml of saturated sodium chloride solution[2]. The ethyl acetate phase is dried over $Na_2SO_4$, filtered and concentrated to dryness in a rotary evaporator.

[2]To recover mandelic acid, these aqueous phases are combined, adjusted to pH=0–1 using conc. hydrochloric acid and extracted with 3·20 ml of ethyl acetate. The combined organic phases are washed with 10 ml of saturated sodium chloride solution, separated from the aqueous phase, dried over $Na_2SO_4$ and concentrated to dryness. The colorless residue is recrystallized from water.

The oily residue is treated with a solution of 310 mg of NaOH in 25 ml of water and stirred at room temperature for 15 hours.

After the reaction time is complete, the clear solution is adjusted to pH 4.5 using 2N hydrochloric acid and stirred for 1 hour, and the colorless precipitate is filtered off with suction and dried to constant weight.

Yield (compound Ib): 920 mg (80% of theory) $[\alpha]_D^{20} = -138°$ (c=1, 0.1N HCl)

Yield (L(+)mandelic acid): 840 mg (86% of theory) $[\alpha]_D^{20} = +154.8°$ (c=5, H$_2$)

The compounds of the formulae Ia and Ib were obtained from the compounds of the formulae VIIIa and VIIb analogously to Example 9a and b.

The following reaction scheme illustrates the reaction sequence described:

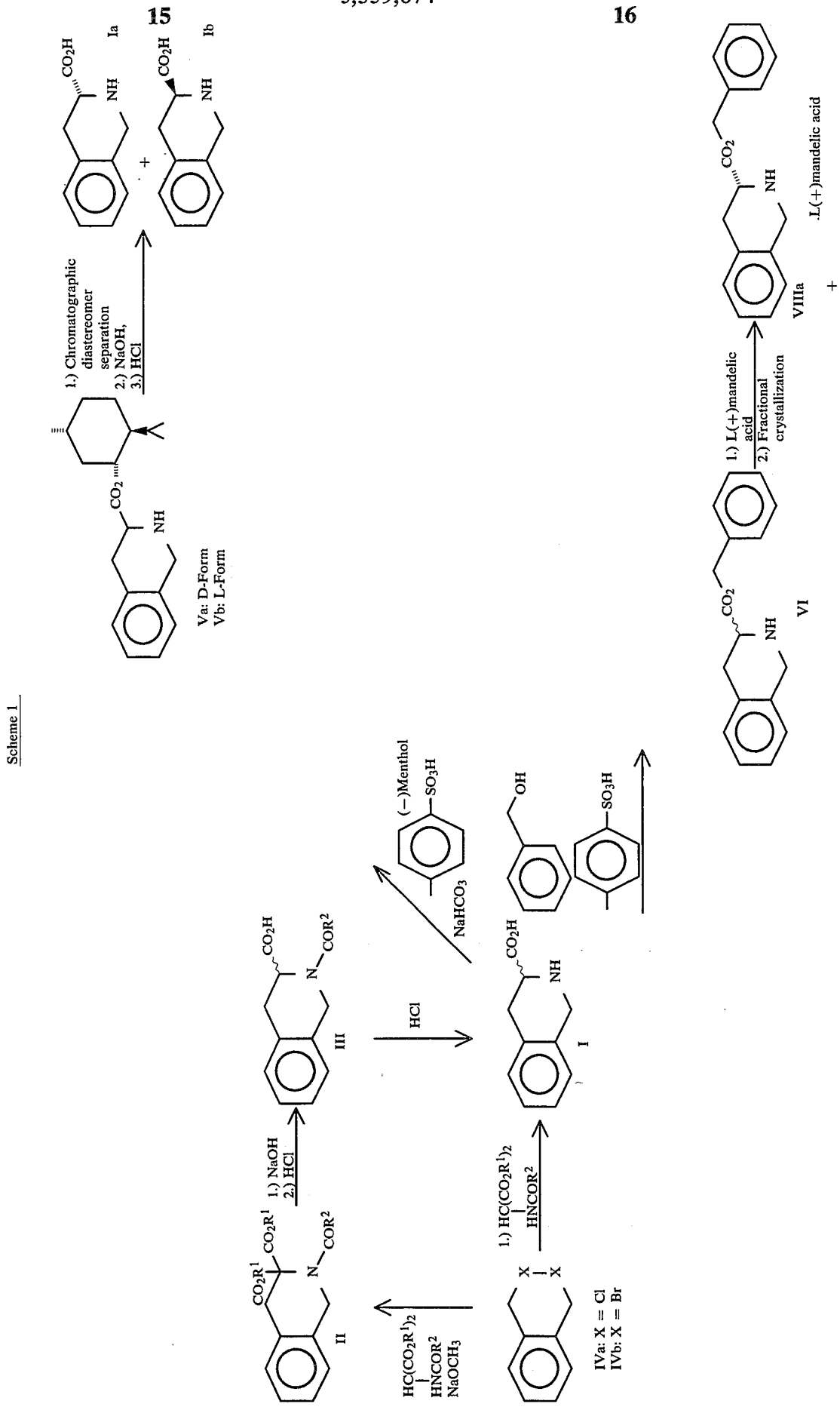
Scheme 1

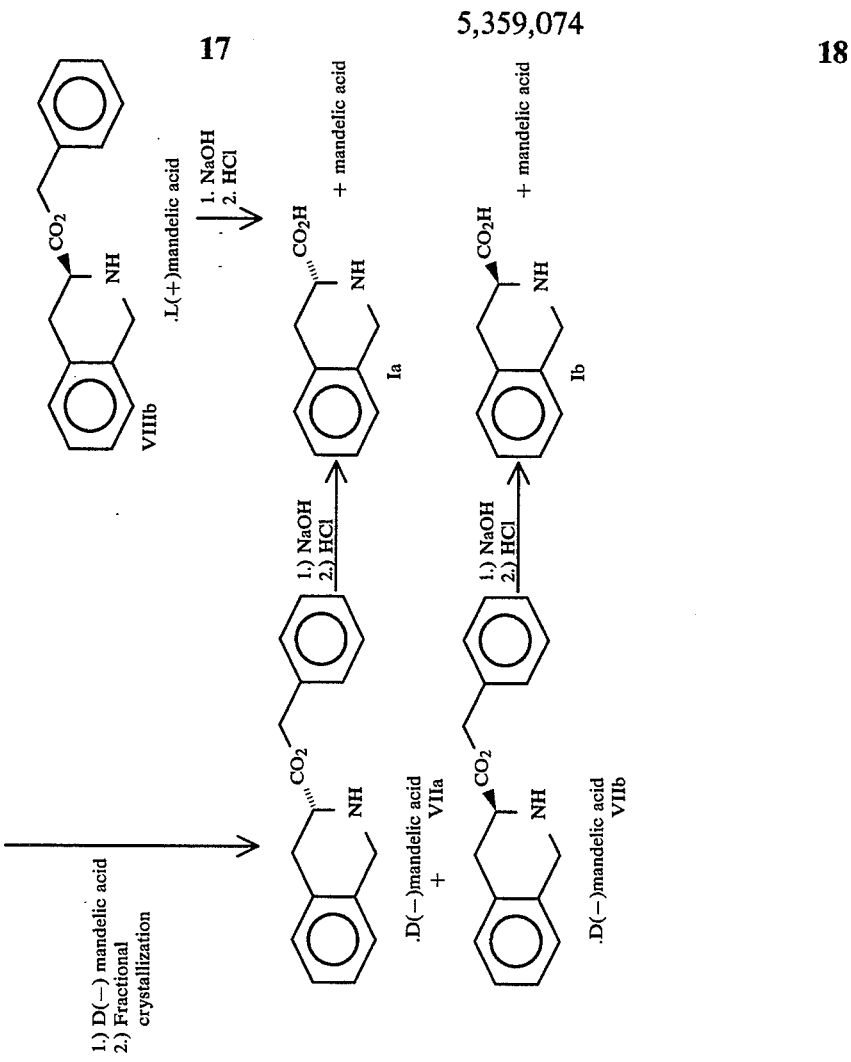

We claim:

1. A compound of the following formula: $C_1$-$C_4$ Dialkyl 1,2,3,4-tetrahydroisoquinoline-N-acyl-3,3-dicarboxylates.

2. A compound of the following formula: Dimethyl 1,2,3,4-tetrahydroisoquinoline-N-acyl-3,3-dicarboxylate.

3. A compound of the following formula: Benzyl (D)-1,2,3,4-tetrahydroisoquinoline-3-carboxylate (D)-mandelate.

4. A compound of the following formula: Benzyl (L)1,2,3,4-tetrahydroisoquinoline-3-carboxylate (D)-mandelate.

5. A compound of the following formula: Benzyl (D)-1,2,3,4-tetrahydroisoquinoline-3-carboxylate (L)-mandelate.

6. A compound of the following formula: Benzyl (L)-1,2,3,4-tetrahydroisoquinoline-3-carboxylate (L)-mandelate.

7. A compound of the following formula: (—)-Menthyl (D,L)-1,2,3,4-tetrahydroisoquinoline-3-carboxylate.

8. A compound of the following formula: (—)-Menthyl (D)-1,2,3,4-tetrahydroisoquinoline-3-carboxylate.

9. A compound of the following formula: (—)-Menthyl (L)-1,2,3,4-tetrahydroisoquinoline-3-carboxylate.

* * * * *